(12) United States Patent
Capuzzi et al.

(10) Patent No.: US 11,039,994 B2
(45) Date of Patent: *Jun. 22, 2021

(54) MIXTURES OF PELARGONIC ACID ESTERS

(71) Applicant: Novamont S.p.A., Novara (IT)

(72) Inventors: Luigi Capuzzi, Novara (IT); Francesca Digioia, Barengo (IT); Vanessa Bramati, Lainate (IT); Federica Carlomagno, Saronno (IT); Alessandra Cominetti, Agnadello (IT)

(73) Assignee: NOVAMONT S.P.A., Novara (IT)

( * ) Notice: Subject to any disclaimer, the term of this patent is extended or adjusted under 35 U.S.C. 154(b) by 194 days.

This patent is subject to a terminal disclaimer.

(21) Appl. No.: 15/758,061

(22) PCT Filed: Sep. 7, 2016

(86) PCT No.: PCT/EP2016/071109
§ 371 (c)(1),
(2) Date: Mar. 7, 2018

(87) PCT Pub. No.: WO2017/042231
PCT Pub. Date: Mar. 16, 2017

(65) Prior Publication Data
US 2018/0177698 A1 Jun. 28, 2018

(30) Foreign Application Priority Data
Sep. 8, 2015 (IT) .................. 102015000049610

(51) Int. Cl.
*A61K 8/37* (2006.01)
*A61K 8/92* (2006.01)
*A61Q 1/00* (2006.01)
*A61Q 1/06* (2006.01)
*A61Q 1/12* (2006.01)
*A61Q 17/04* (2006.01)
*A61Q 19/00* (2006.01)

(52) U.S. Cl.
CPC ............... *A61K 8/375* (2013.01); *A61K 8/92* (2013.01); *A61Q 1/00* (2013.01); *A61Q 1/06* (2013.01); *A61Q 1/12* (2013.01); *A61Q 17/04* (2013.01); *A61Q 19/00* (2013.01); *A61K 2800/5922* (2013.01)

(58) Field of Classification Search
None
See application file for complete search history.

(56) References Cited

U.S. PATENT DOCUMENTS

2004/0126350 A1  7/2004  Blin et al.
2015/0209429 A9  7/2015  Lathrop et al.

OTHER PUBLICATIONS

"Sunscreen SPF 50+", GNPD, Mintel; Oct. 31, 2012; XP-002753094.
"Bb. Shine on (and on . . . ) Finishing Spray", GNPD, Mintel; Jun. 30, 2011; XP-002753095.

*Primary Examiner* — Bethany P Barham
*Assistant Examiner* — Barbara S Frazier
(74) *Attorney, Agent, or Firm* — Polsinelli PC

(57) ABSTRACT

Mixture of at least two esters selected from neopentylglycol dipelargonate, glycerol tripelargonate, pentaerythritol tetrapelargonate, and use thereof in cosmetic compositions for the care, the make-up, the protection from the sun and for the cleansing of the skin and skin appendages.

19 Claims, No Drawings

MIXTURES OF PELARGONIC ACID ESTERS

CROSS REFERENCE TO RELATED APPLICATIONS

This application is a National Phase filing under 35 U.S.C. § 371 of PCT/EP2016/071109 filed on Sep. 7, 2016; and this application claims priority to application Ser. No. 10/201, 5000049610 filed in Italy on Sep. 8, 2015 under 35 U.S.C. § 119. The entire contents of each application are hereby incorporated by reference.

DESCRIPTION

This invention relates to mixtures of at least two esters selected from neopentyl glycol dipelargonate, glycerol tripelargonate and pentaerythritol tetrapelargonate, their use in cosmetic compositions and cosmetic compositions containing them.

In the cosmetics sector increasing attention has been paid to the identification of new ingredients of natural and renewable origin, having a low environmental impact and at the same time having excellent functional and sensory properties.

Cosmetic compositions find application in care of the skin, hair, in make-up and in hygiene products, and commonly contain a lipophilic component which depending on the product helps to ensure excellent detergency, hydration and softness, helps lubrication and applicability of the product, the dispersion of sun filters, colouring agents, active agents and additives and/or acts as a binder, encouraging adhesion between the various ingredients, for example acting as a binder in cosmetic compositions such as eye shadows and compacted powders.

It has now been observed that esters of pelargonic acid which can be obtained from renewable sources with polyols such as neopentyl glycol, glycerol and pentaerythritol, when used in a mixture together, have particular lubricating abilities and impart a soft and smooth appearance to the skin; they are also capable of maintaining skin moisture because of their ability to form a barrier which slows down the loss of water from the skin. They also have a binding action for powders and have an excellent ability to disperse sun filters, pigments, active ingredients and other additives.

Binary and ternary mixtures of neopentyl glycol dipelargonate, glycerol tripelargonate and pentaerythritol tetrapelargonate are therefore suitable for use as ingredients of the lipophilic component of compositions for cosmetic use, i.e. for the preparation of products intended for application to the outer surface of the human body (epidermis, lips and cutaneous annexes) in order exclusively or mainly to clean them, perfume them, modify their appearance, protect them, maintain them in a good condition or correct body odours. By suitably altering the ratios between the esters in the mixture and their quantities in the formulation they make it possible to obtain anhydrous compositions and aqueous compositions having excellent properties which are suitable for an extensive range of applications.

The object of this invention is therefore a mixture of at least two esters selected from neopentyl glycol dipelargonate, glycerol tripelargonate, pentaerythritol tetrapelargonate and their use in cosmetic compositions.

According to an advantageous aspect of the invention the esters present in the said mixtures (i.e. neopentyl glycol dipelargonate, glycerol tripelargonate, pentaerythritol tetrapelargonate) are prepared from pelargonic acid from renewable sources, obtained for example by processes of the oxidative cleavage of vegetable oils, fatty acids and their derivatives, which may or may not be modified. Preferred examples of renewable sources of pelargonic acid are vegetable oils from sunflowers, brassicaceae or thistles (such as *Cynara cardunculus* and *Silybum marianum*). Particularly preferred sources of pelargonic acid are represented by vegetable oils having a high oleic or erucic acid content.

The said pelargonic acid is preferably obtained by oxidative cleavage processes in which inorganic and organic peroxides, peracids, nitric acid, permanganates, periodates, $O_2$, $O_3$ or their gaseous mixtures are used as oxidising agents.

Oxidative cleavage processes in which peroxides such as hydrogen peroxide and $O_2$ or mixtures containing $O_2$ are used as oxidising agents are preferred. Specific examples are the oxidative cleavage processes described in applications WO 94/10122, WO 07/039481, WO 2008/138892, WO 2011/080296, WO 2011/080297 or WO 2013/079849.

The abovementioned esters are preferably each prepared from high purity pelargonic acid, preferably higher than 95%, more preferably higher than 98%, and a polyol selected from neopentyl glycol, glycerol or pentaerythritol, through an esterification reaction which is advantageously performed in the absence of catalyst.

The said esterification is advantageously carried out in the presence of a molar excess of pelargonic acid with respect to the moles of polyol, preferably of or greater than 30% and less than 70%, operating at temperatures typically between 180 and 240° C., preferably 200-210° C. The water forming during the esterification reaction is advantageously removed from the reaction environment, for example by applying a gradual reduction in pressure; at the end of the reaction the excess acid is removed, preferably by evaporation. The ester so obtained can advantageously undergo purification treatments according to processes known to those skilled in the art, for example using activated carbons and decolouring earths with a view to removing any colouration, odour and residual acidity. Examples of decolouring earths which may be used, including in combination with activated carbons, are Grade F-118FF, Grade F76 (marketed by BASF), Minclear N100, Minclear E100 and Pansil 2 (marketed by Tolsa).

In comparison with esters obtained by the common esterification procedures catalysed by metals, for example tin, the esters obtained by operating in accordance with the procedure described above do not contain metal residues which might influence their organoleptic properties (e.g. colour, odour) and their stability, and the toxicological properties of the finished cosmetic products. They therefore have the particular advantage of a lesser inorganic material content and require simplified preliminary treatments for use in the cosmetic environment.

Cosmetic compositions comprising mixtures of at least two of the said pelargonic acid esters described above are another object of the invention.

The said compositions may, for example, be prepared by adding the said pelargonic acid esters to the other ingredients separately (one at a time) or simultaneously, before they are mixed together.

The cosmetic compositions according to the invention may contain from 0.1% to 99% by weight of the said mixtures with respect to the total weight of the composition. These may take the form of lipophilic cosmetic compositions (i) or aqueous cosmetic compositions (ii), and contain in each case a characteristic optimum amount of the said mixtures.

Lipophilic Cosmetic Compositions (i)

The mixtures according to the invention are particularly suitable as ingredients of the oily component of cosmetic compositions intended for the preparation of oils, butters, concealers, lipsticks, sun protection products, or as binding agents in compositions in the form of compact powders such as eye shadow, blushers, face powders and foundation powders. One preferred aspect of the invention therefore relates to lipophilic cosmetic compositions comprising a mixture of at least two esters selected from neopentyl glycol dipelargonate, glycerol tripelargonate, pentaerythritol tetrapelargonate.

The compositions of a lipophilic nature according to the invention comprise an oily component which in turn comprises or advantageously consists of the said mixture of at least two esters selected from neopentyl glycol dipelargonate, glycerol tripelargonate, pentaerythritol tetrapelargonate according to the invention. The said lipophilic compositions advantageously comprise up to 99% by weight, preferably up to 95%, of the said mixture with respect to the weight of the cosmetic composition. Examples of lipophilic compositions of this type are described in Italian application, No. 102015000049554, incorporated here as a reference.

In addition to the abovementioned mixture, the said oily component may also contain other oils of plant, animal, mineral and/or synthetic origin, preferably selected from esters, amides, ethers, alcohols and hydrocarbons of natural and/or synthetic origin, silicone oils or their mixtures.

Possible examples of esters of natural origin are triglycerides of saturated or unsaturated fatty acids, such as for example triglycerides of C8 and C10 acids, or their mixtures such as for example those present in vegetable oils. Suitable vegetable oils are for example olive oil, sunflower oil, maize oil, soya oil, castor oil, apricot oil, avocado oil, almond oil, macadamia oil, jojoba oil or karite oil.

Esters of synthetic origin are for example esters of linear and branched carboxylic acids with monoalcohols, such as isononyl isononanoate, isopropyl myristate, 2-ethy hexyl palmitate, isodecyl neopentanoate, isostearyl neopentanoate, 2-octyldodecyl stearate, 2-octyldodecyl erucate or isostearyl isostearate, diisostearyl maleate, C12-15 alkyl benzoate; esters of C7-C10 chain fatty acids with fatty alcohols; hydroxylated esters, such as isostearyl lactate, octyl hydroxystearate, octyldodecyl hydroxystearate; esters of polyols, such as propylene glycol dioctanoate, neopentyl glycol diheptanoate or diethylene glycol diisononanoate and pentaerythrityl tetraisostearate.

One example of an ether is dicaprilyl ether. One example of an amide is dibutyl lauroyl glutamide.

Other examples of oils include fatty alcohols such as octyldodecanol, hexyldodecanol, isostearyl alcohol.

Hydrocarbon oils of natural origin are for example terpene hydrocarbons such as squalene and squalane; hydrocarbon oils of mineral or synthetic origin are for example liquid paraffin and its derivatives such as isoparaffins (e.g. isododecane, isohexadecane, polydecene hydrogenate) and cycloparaffins.

The silicone oils are synthetic compounds based on silicon; they may be volatile or non-volatile, linear or cyclic. Examples of silicone oils are polysiloxanes and their derivatives comprising for example alkyl, alkoxyl or phenyl groups; silicone oils typically used include the polydimethylsiloxanes (Dimethicone), Amodimethicone, Cyclomethicones such as Cyclopentasiloxane and Cyclohexasiloxane, Amino Bispropyl Dimethicone, Aminopropyl Dimethicone, Amodimethicone hydroxystearate, Behenoxy-Dimethicone, C30-45 Alkyl Dimethicone, C24-28 Alkyl Dimethicone, C30-45 Alkyl Methicone, Cetearyl Methicone, Cetyl Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone.

The lipophilic compositions according to the invention may advantageously also comprise one or more waxes in quantities of typically between 0.1 and 35% by weight with respect to the total weight of the composition. Those skilled in the art will be readily able to adjust the quantities and types of waxes which are to be used on the basis of their desired effect in the cosmetic composition.

By the term "wax" is meant a lipophilic component which is solid at ambient temperature (25° C.) and atmospheric pressure; the said component imparts viscosity, plasticity and strength to the cosmetic compositions containing it, which are therefore suitable for preparation in solid form, for example as sticks.

Waxes which are suitable for use in the cosmetic compositions according to the invention are all the waxes typically used in cosmetic compositions, which may be of natural and/or synthetic origin. Examples of natural waxes are beeswax or cera alba, carnauba wax, candelilla wax, Japan wax, rice wax, waxes deriving from hydrogenated oils, such as jojoba oil or sunflower or coconut oils, esters of long chain fatty acids with long chain mono-alcohols or their glycerides, such as cetyl palmitate, cetyl stearate, palmitic and stearic triglycerides.

Examples of mineral or synthetic waxes are lignite wax, microcrystalline wax, paraffin, ozokerite, ceresin, synthetic beeswax, lanolin and their ethers with polypropylene glycols, polyethylene waxes, esters of fatty acids having a melting point over 25° C., polyamides, and cetyl esters. Silicone waxes such as alkyl or alkoxy-dimethicones or poly(di)methylsiloxanes having a high molecular weight may also be used.

Advantageously the cosmetic compositions according to the invention comprise one or more components deriving from the insaponifiable fraction of vegetable oils (for example carotenoids, xanthophylls, tocopherols, phytosterols, aliphatic and terpene alcohols). Vitamins and active ingredients of a lipophilic nature may also be present dissolved in the oily component.

According to a particularly preferred embodiment the invention relates to cosmetic compositions in lipophilic form comprising, with respect to the weight of the cosmetic composition:
a) from 50 to 99% by weight, preferably from 55 to 95%, more preferably from 40 to 80%, of an oily component comprising a mixture of at least two esters selected from neopentyl glycol dipelargonate, glycerol tripelargonate and pentaerythritol tetrapelargonate;
b) from 1 to 35% by weight, preferably from 5 to 30%, more preferably from 7 to 20%, of one or more waxes;
c) from 0 to 30% by weight, preferably from 0.1 to 20% by weight, more preferably from 0.1 to 15%, of one or more colouring agents;
d) from 0 to 3%, preferably from 0.05 to 2% by weight of vitamins and/or antioxidants;
e) from 0 to 2% by weight, preferably from 0.01 to 1%, of one or more preservatives.

The said composition is particularly suitable for the preparation of lipsticks, butters and balms for the lips, concealers, foundation creams and cast and stick eye shadows.

The compositions according to the invention may advantageously also comprise one or more sun filters in quantities of preferably between 0.05% and 35% by weight, preferably between 0.1 and 30%, with respect to the weight of the cosmetic composition.

Sun filters have the function of protecting skin and/or hair from UVA/UVB radiation. These include for example filters or physical screens with reflecting properties such as for example zinc oxide and titanium dioxide, either in the form of nanomaterials or having particles of larger size, silica, kaolin, iron and/or magnesium oxides, and chemical filters, typically organic molecules capable of absorbing and converting the energy of ultraviolet radiation such as cinnamates, benzoimidazoles, benzophenones, benzylidene camphorate, PABA and its derivatives, salicylates, anthranylates, dibenzoyl methanes, octocrylene, triazines such as octyltriazone, bis-ethylhexyloxyphenol methoxyphenyl triazine and diethyl hexyl butamido triazone, natural antioxidants such as vitamin C and vitamin E or synthetic vitamins, such as Tinogard TT, or their combinations.

Physical and chemical filters may be of natural origin (such as for example gamma orizanol) or synthetic, and be used alone or more advantageously in combination.

Specific examples of sun filters suitable for use in the compositions according to the invention are octyl-methoxy-cinnamate, 2-ethyl-hexyl-4-dimethylaminobenzoate, butyl-methoxy-dibenzoylmethane, octyl triazone, diethyl hexylbutamido triazone, ethyl hexyl salicylate, zinc oxide, titanium dioxide, or their combinations.

According to a particularly preferred embodiment the invention relates to a lipophilic cosmetic composition comprising, with respect to the weight of the cosmetic composition:
 a) from 50 to 99% by weight, preferably from 50 to 90%, of an oily component comprising a mixture of at least two esters selected from neopentyl glycol dipelargonate, glycerol tripelargonate and pentaerythritol tetrapelargonate and their mixtures;
 b) from 0.05 to 35% by weight, preferably from 0.1 to 30%, of one or more sun filters;
 c) from 0 to 30% by weight, preferably from 5 to 30%, more preferably from 7 to 20%, of one or more waxes;
 d) from 0 to 30% by weight, preferably from 0.1 to 3%, of one or more colouring agents;
 e) from 0 to 2% by weight, preferably from 0.01 to 1%, of one or more preservatives.

The said composition is particularly suitable for the preparation of sun protection products, for example sun protection sticks, oils and butters.

The compositions according to the invention may advantageously also comprise one or more polyolefins, acrylic derivatives, polyamide and/or polyester oligomers, for example selected from polybutylene or polyisobutylene.

Lipophilic compositions comprising from 15 to 85% by weight of the aforesaid oligomers, and from 5 to 65% by weight, preferably between 10 and 35% by weight, of oily component with respect to the total weight of the cosmetic composition are preferred. The said compositions also advantageously comprise suspended powders, colouring agents and antioxidants. Cosmetic compositions of this type are particularly suitable for the preparation of cosmetics such as lip gloss.

By "oligomers" are typically meant oligomers and polymers having a molecular weight of below 1000 g/mole, which are liquid at ambient temperature (25° C.) and atmospheric pressure, which are responsible for providing brightness and tack to the cosmetic composition.

Suitable oligomers are selected from the group comprising polybutylenes, polyisobutylenes and hydrogenated polyisobutylenes, polydecenes and hydrogenated polydecenes, polyethylene, polyamides, polyesters. Preferred oligomers are selected from polybutylene, polyisobutylene and/or polyamides.

According to a particularly preferred embodiment the invention relates to a lipophilic cosmetic composition comprising, with respect to the weight of the cosmetic compositions:
 a) from 15 to 85% by weight, preferably from 20 to 80%, of one or more oligomers;
 b) from 5 to 65% by weight, preferably from 10 to 35%, of an oily component comprising at least one ester selected from neopentyl glycol dipelargonate, glycerol tripelargonate and pentaerythritol tetrapelargonate and their mixtures;
 c) from 0 to 15% by weight, preferably from 2 to 5%, of one or more flow modifiers having suspension powers;
 d) from 0 to 20% by weight, preferably from 0.1 to 15%, of one or more colouring agents;
 e) from 0 to 5% by weight, preferably from 0.1 to 3%, of one or more waxes;
 f) from 0 to 3% by weight, preferably from 0.05 to 2%, of vitamins and/or antioxidants;
 g) from 0 to 2% by weight, preferably from 0.01 to 1%, of one or more preservatives.

The said composition is particularly suitable for the preparation of lip gloss.

The cosmetic compositions according to the invention have different characteristics depending upon the composition of the mixture of pelargonic acid esters. For example binary mixtures of neopentyl glycol dipelargonate and glycerol tripelargonate form a thin film and impart an evanescent after-feel to the lipophilic cosmetic compositions containing them.

Binary mixtures of neopentyl glycol dipelargonate and pentaerythritol tetrapelargonate form a thin but prominent film, and impart good flow and brightness characteristics to the lipophilic cosmetic compositions.

Binary mixtures of glycerol tripelargonate and pentaerythritol tetrapelargonate form a prominent film and provide the lipophilic cosmetic compositions containing them with a brilliant effect, a light and non-unctuous touch, good flow and comfort. Thanks to the good dispersion of UVA/UVB sun filters they are particularly suitable for application in sun protection products.

Ternary mixtures of neopentyl glycol dipelargonate, glycerol tripelargonate and pentaerythritol tetrapelargonate are film-forming and provide the cosmetic compositions with excellent flow and a brilliant finish, great comfort and are non-unctuous. They offer excellent dispersion of pigments and UVA/UVB sun filters and are therefore suitable for application in sun protection products.

According to one particularly advantage aspect the invention relates to powder-based lipophilic compositions, that is those mainly comprising one or more powder components selected from talc, mica, kaolin, silica, starches, silica-coated mica and talc, titania, titania-coated mica and talc, starches, apatite, perlite, polymers such as for example nylon and polyethylene, copolymer microspheres, silicone resin microbeads, or their mixtures. The said powder-based compositions comprise one or more binding agents which, in turn, comprise or advantageously consist of a mixture of at least two esters selected from neopentyl glycol dipelargonate, glycerol tripelargonate and pentaerythritol tetrapelargonate. The compositions according to this aspect advantageously also comprise texturising agents, colouring agents and possibly perfume and a preservative system. The said powder-based compositions advantageously comprise from 0.1% to 20% by weight, more preferably from 0.1% to 15% by weight, of the said mixture with respect to the weight of the cosmetic composition. They advantageously comprise more than 35% by weight, preferably more than 40% by weight and more preferably more than 50% by weight of powder component. Examples of compositions of this type are described in patent application No. 102015000049579, incorporated here as a reference. These compositions find application in products such as eye shadow, blusher, face powder, opaque make-up, loose and compacted powders.

It has been observed that the preparation of powder-based compositions containing a single ester of pelargonic acid with neopentyl glycol, glycerol or pentaerythritol necessarily requires the addition of other binding agents in order to achieve a degree of adhesion between the components and spreadability, which render them acceptable for final users. Conversely, when two or more of these esters are used as ingredients in the mixture, they show a surprising binding, lubricating, emollient and hydrating effect at the same time; the resulting compositions achieve a degree of spreadability and comfort, such that the further addition of binding agents is not required.

For example powder-based cosmetic compositions containing a binary mixture of neopentyl glycol dipelargonate and glycerol tripelargonate provide a light film and good spreadability. Powder-based cosmetic compositions containing a binary mixture of neopentyl glycol dipelargonate and pentaerythritol tetrapelargonate provide a light but comfortable film and have good spreadability.

Anhydrous cosmetic compositions containing a binary mixture of glycerol tripelargonate and pentaerythritol tetrapelargonate provide a more persistent and comfortable film, which is not unctuous, and have good spreadability.

Powder-based cosmetic compositions containing a ternary mixture of neopentyl glycol dipelargonate, glycerol tripelargonate and pentaerythritol tetrapelargonate provide a very persistent and comfortable film, which is non-unctuous, and have excellent spreadability. The said powder-based compositions may optionally comprise other ingredients of an oily or waxy type, in addition to the mixtures according to the invention, as binding agents. For example the oils listed above as being typical ingredients of the oily component of anhydrous compositions, and all the waxes typically used in cosmetic compositions, have a binding action.

Examples of binding agents which might be advantageously added to the powder-based compositions, together with the mixtures of esters according to the invention, are hydrocarbons such as polydecene, esters such as octyldodecyl stearoyl stearate, triglycerides such as the triglyceride of capric/caprylic acids, fluid silicones and lanolin derivatives. Salts of fatty acids such as magnesium stearate, zinc stearate, calcium stearate, lithium stearate, aluminium stearate and their mixtures are also advantageously used in combination with the mixture of esters according to the invention in the said powder-based compositions. According to a preferred embodiment the invention relates to a powder-based cosmetic composition in anhydrous form comprising, with respect to the weight of the cosmetic composition:
  (a) from 35 to 99% by weight of powder,
  (b) from 1 to 20% by weight, preferably from 3 to 15% by weight, of a binding component comprising a mixture of at least two esters selected from neopentyl glycol dipelargonate, glycerol tripelargonate, pentaerythritol tetrapelargonate and their mixtures,
  (c) from 0 to 30% by weight of one or more texturising agents,
  (d) from 0 to 15% by weight, preferably from 2 to 10%, of one or more colouring agents,
  (e) from 0 to 15% by weight, preferably from 1 to 15%, more preferably from 5 to 15% by weight, of a salt of a fatty acid,
  (f) from 0 to 2% by weight, preferably from 0.01 to 1%, of one or more preservatives.

Examples of texturising agents advantageously used in the aforesaid compositions are starches, starches modified with hydrophobic groups, polymers such as polyamides, polyurethanes and polyacrylates, in particular polymethyl methacrylates. The lipophilic cosmetic compositions according to this invention preferably contain water in quantities not exceeding 20%; preferably the water content is less than 5% with respect to the weight of the cosmetic composition.

Aqueous Cosmetic Compositions (ii)

The mixtures according to the invention are also particularly suitable as ingredients in aqueous cosmetic compositions, for example in the form of oil-based or water-based emulsions, in the form of micro-emulsions or water-lipid dispersions.

The said aqueous cosmetic compositions preferably comprise more than 20%, preferably more than 35%, and even more preferably more than 50% by weight of a hydrophilic or aqueous component comprising water. Together with the aqueous component these also contain a lipophilic component which in turn comprises or advantageously consists of a mixture of at least two esters selected from neopentyl glycol dipelargonate, glycerol tripelargonate and pentaerythritol tetrapelargonate. The said aqueous compositions advantageously comprise from 0.1% to 50% by weight, more preferably from 0.1% to 35% by weight, of the said mixtures with respect to the weight of the cosmetic composition. Examples of compositions of this type are described in Italian application No. 102015000049538, incorporated here as a reference.

In addition to the mixtures of esters of pelargonic acid according to the invention, the said lipophilic component may comprise other components in liquid form at ambient temperature (25° C.) and atmospheric pressure, such as oils of plant, animal, mineral and/or synthetic origin, preferably selected from esters, amides, ethers, alcohols and hydrocarbons of natural and/or synthetic origin, silicone oils or their mixtures. Typical examples are the oils listed above as typical ingredients of the oily component of the lipophilic compositions.

According to a preferred aspect of the invention, the mixtures of esters of pelargonic acid in question are suitable for the preparation of aqueous cosmetic compositions in the form of oil-based emulsions (water in oil, W/O), or water-based emulsions (oil in water O/W), which may occur in multiple form (for example W/O/W or O/W/O).

In the case of emulsions the lipophilic component may comprise other components in solid or paste form at ambient temperature (25° C.) and atmospheric pressure, such as butters and/or waxes, in addition to the mixtures according to the invention. Examples of butters are Karite butter, cocoa butter, cupuacu butter. Suitable waxes are all the waxes commonly used in cosmetic compositions.

Cosmetic compositions in the form of an oil-based emulsion according to the invention advantageously comprise up to 50% by weight, preferably up to 35%, more preferably up to 25% by weight, of the said mixtures with respect to the weight of the cosmetic composition. A preferred example of oil-based emulsions according to this invention are silicone-based emulsions (W/Si) in which the lipophilic component comprises one or more silicone oils and two or more of the pelargonic acid esters specified above.

Binary mixtures of glycerol tripelargonate and pentaerythritol tetrapelargonate, or ternary mixtures of neopentyl glycol dipelargonate, glycerol tripelargonate and pentaerythritol tetrapelargonate are preferred and can be used as the sole ingredient of the lipophilic component.

Binary mixtures comprising neopentyl glycol dipelargonate advantageously comprise up to 15%, preferably up to 10%, more preferably up to 5% by weight with respect to the weight of the cosmetic composition and are preferably used together with other oils, butters or waxes. According to a preferred embodiment the invention relates to an aqueous cosmetic composition in the form of an oil-based emulsion comprising, with respect to the weight of the cosmetic composition:
  (a) from 35 to 80% by weight, of an aqueous phase;
  (b) from 10% to 50% by weight, preferably from 10 to 35% of a lipophilic component comprising a mixture of at least two esters selected from neopentyl glycol dipelargonate, glycerol tripelargonate and pentaerythritol tetrapelargonate;
  (c) from 0.3% to 15% by weight of one or more emulsifiers with an HLB of preferably between 3 and 6.

Typically, the said aqueous phase comprises from 60 to 80% by weight, and the said lipophilic component comprises 25-35% by weight of the cosmetic composition.

The said aqueous phase may also contain chelating agents, such as for example ethylenediamine tetraacetic acid and its sodium salts (e.g. bisodium, trisodium and tetrasodium salts), sodium chloride, magnesium sulfate and other stabilisers, preservatives, active ingredients and hydrating agents.

The compositions in the form of oil-based emulsions according to this embodiment are for example suitable for the preparation of creams, sun protection products, serums, foundation creams, concealers and mascaras.

The cosmetic compositions in the form of water-based emulsion according to the invention advantageously comprise up to 35%, preferably up to 20% by weight of the said mixture of at least two esters selected from neopentyl glycol dipelargonate, glycerol tripelargonate and pentaerythritol tetrapelargonate.

The binary mixtures according to the invention comprising neopentyl glycol dipelargonate are preferred and may be used as the sole ingredient of the lipophilic component of these compositions.

Binary mixtures of glycerol tripelargonate and pentaerythritol tetrapelargonate or ternary mixtures of neopentyl glycol dipelargonate, glycerol tripelargonate and pentaerythritol tetrapelargonate advantageously comprise up to 15%, preferably up to 10%, more preferably up to 5% by weight with respect to the weight of the said cosmetic compositions and are preferably used together with other oils, butters or waxes.

According to a preferred embodiment the invention relates to an aqueous cosmetic composition in the form of a water-based emulsion comprising, with respect to the weight of the cosmetic composition:
  (a) from 60 to 90% by weight of an aqueous phase;
  (b) from 0.5% to 40% by weight, preferably from 1 to 20%, of a lipophilic component comprising a mixture of at least two esters selected from neopentyl glycol dipelargonate, glycerol tripelargonate and pentaerythritol tetrapelargonate, or a mixture thereof;
  (c) from 5% to 15% by weight of one or more emulsifiers with an HLB of preferably between 6 and 12.

The compositions in the form of water-based emulsion, according to this embodiment, are for example suitable for the preparation of creams, milks, serums, butters, sun protection products, hair products such as balms, masks, leave-ons and make-up products, such as foundation creams, mascaras, concealers, and products for making up the lips.

Typical emulsifying agents used in compositions according to the invention have long or medium-length alkyl chains (generally longer than C12), and may be anionic, cationic, amphoteric or non-ionic.

The said emulsifying agents may be selected for example from the group comprising monoglycerides of fatty acids, sorbitan esters (for example monoesters, diesters, triesters and their mixtures) which may optionally be ethoxylated, saccharose esters, protein condensates with fatty acids, polyglycerols and/or their esters with fatty acids, ethers of glucose and/or polyglucose with fatty alcohols, lecithin and/or hydrogenated lecithin, ethoxylated fatty alcohols, ethoxylated fatty acids (for example PEG-100 stearate), soaps such as triethanolamine stearate, ethoxylated and non-ethoxylated phosphoric esters (for example potassium cetyl phosphate).

Emulsifying agents suitable for oil-based emulsions typically have unsaturated, branched or substituted alkyl chains, such as for example the oleic, isostearyl, ricinoleic and hydroxystearyl chains.

Emulsifying agents suitable for water-based emulsions typically have saturated and linear chains, such as for example stearyl and palmitoleic chains.

According to another aspect the cosmetic compositions in the form of water-based emulsion according to the invention advantageously comprise up to 15%, preferably up to 10% by weight of the said mixture of at least two esters selected from neopentyl glycol dipelargonate, glycerol tripelargonate and pentaerythritol tetrapelargonate.

According to a particularly preferred aspect, the invention relates to aqueous cosmetic compositions comprising, with respect to the total weight of the cosmetic composition:
  (a) from 60 to 90% by weight of an aqueous component;
  (b) from 0.5% to 15% by weight, preferably from 1 to 10%, of a lipophilic component comprising a mixture of at least two esters selected from neopentyl glycol dipelargonate, glycerol tripelargonate and pentaerythritol tetrapelargonate;
  (c) from 8% to 40% by weight of one or more surfactants.

Of these compositions those preferred are those in which the lipophilic component comprises binary mixtures of neopentyl glycol dipelargonate and glycerol tripelargonate, which may constitute up to 20%, preferably from 0.1% to 15%, more preferably from 0.1% to 12% with respect to the weight of the lipophilic component. Compositions in which the lipophilic component also comprises vegetable oils in addition to the abovementioned mixtures of esters, are also preferred.

Binary mixtures of glycerol tripelargonate and pentaerythritol tetrapelargonate, neopentyl glycol dipelargonate and pentaerythritol tetrapelargonate, or the ternary mixture of neopentyl glycol dipelargonate, glycerol tripelargonate and pentaerythritol tetrapelargonate, may advantageously comprise up to 10% by weight, preferably from 0.1% to 8%, more preferably from 0.1% to 6% of the lipophilic component of the said compositions.

In such aqueous cosmetic compositions the said surfactants have the function of reducing surface tension, encouraging detergency; they may or may not have a foam-generating function and may be non-ionic, anionic, amphoteric or cationic.

Typical surfactants used in compositions according to the invention typically have short or medium-length alkyl chains (generally shorter than C14), such as for example those of capric, caprylic and lauric acids.

They may be selected for example from the group comprising: alkyl sulfates and/or alkyl ether sulfates, preferably of Na, Mg, Zn or ammonium (NH4), monoethanolamine (MEA), triethanolamine (TEA) or monoisopropylamine (MIPA); alkyl ether carboxylates; protein condensates with fatty acids; acyl glutamates; acyl sarcosinates; acyl isothionates; acyl methyl taurates; alkyl sulfosuccinates; soaps; alkyl betaine and alkylamidopropyl betaine; alkyl and alkylamidohydroxy sultaine; alkyl amphoacetates and alkyl amphodiacetates; alkyl amphopropionates and alkyl amphodipropionates; alkyl and alkylamidopropyl aminoxides; polysorbates (e.g. polysorbate 20); monosaccharose esters; alkyl glucosides; quaternary ammonium salts.

Those skilled in the art will readily be able to determine the quantity of surfactant required on the basis of the type of cosmetic product for which the composition is intended. For example, cosmetic compositions intended for the preparation of intimate detergents typically contain a quantity of surfactants comprising from 8 to 10% by weight; shampoos from 10 to 15% by weight; shower foam from 13 to 18% by weight, and bath foam from 18 to 22% by weight. The compositions in the form of a single phase aqueous solution according to this aspect of the invention may advantageously take the form of micro-emulsions; they are suitable, for example, for the preparation of bath foams, shower gels, detergents, shampoos, leave-on products and liquid soaps.

According to another preferred aspect of the invention the said aqueous cosmetic compositions are in two-phase form, or have the aqueous phase separate from the lipophilic phase in two separate layers. Cosmetic products prepared with these compositions typically require mixing before use, giving rise to the formation of temporary emulsions. Preferably the said compositions comprise, with respect to the total weight of the cosmetic composition:

(a) from 50 to 70% by weight of an aqueous phase;
(b) from 30% to 50% of a lipophilic phase comprising a mixture of at least two esters selected from neopentyl glycol dipelargonate, glycerol tripelargonate and pentaerythritol tetrapelargonate.

The said compositions in two-phase form preferably comprise up to 50% by weight, more preferably between 0.1 and 30% by weight, even more preferably between 0.1 and 10% by weight, of the said mixture with respect to the weight of the lipophilic phase.

Compositions in which the lipophilic phase comprises binary mixtures of neopentyl glycol dipelargonate and glycerol tripelargonate, or neopentyl glycol dipelargonate and pentaerythritol tetrapelargonate, which advantageously comprise up to 30% by weight with respect to the weight of the lipophilic phase are preferred.

Compositions in which the lipophilic phase comprises from 0.1 to 15%, more preferably from 0.1 to 10% by weight of binary mixtures of glycerol tripelargonate and pentaerythritol tetrapelargonate, or ternary mixtures of neopentyl glycol dipelargonate, glycerol tripelargonate and pentaerythritol tetrapelargonate are also preferred.

In addition to the mixture of the aforesaid esters of pelargonic acid, the said lipophilic phase preferably comprises mineral and/or silicone oils, for example isododecanes, cyclopentasiloxane, reaction products of propylene oxide with stearyl alcohols (such as polypropylene glycol-15 stearyl ether), vegetable oils such as almond, olive and jojoba oils. The aqueous compositions in two-phase form, according to this aspect of the invention, are suitable for example for the preparation of make-up products.

The cosmetic compositions according to the invention, whether in the form of an anhydrous composition or an aqueous composition, may comprise one or more sun filters, as described above, in the case of anhydrous compositions. The said sun filters are used in quantities of preferably between 0.05% and 35% by weight, preferably between 0.1 and 25%, with respect to the weight of the cosmetic composition.

Thanks to the properties of the pelargonic acid esters present in them, the mixtures according to the invention have the particular advantage that they ensure optimum dispersion and/or dissolution of sun filters, whose stability they may increase when used in an emulsion, and whose protection factor they may help to increase. Additionally, they have shown a higher solubilisation and dispersion rates when compared to some of the commonly used oily solvents/dispersants. They are therefore suitable for use in cosmetic compositions intended for protection from the sun, care of the body and hair, and make-up products having a protective and anti-aging action.

Compositions comprising mixtures comprising pentaerythritol tetrapelargonate and/or glycerol tripelargonate, whose flow and viscosity properties are particularly marked and which are provided with particular emollience, are particularly suitable for this purpose. Mixtures comprising pentaerythritol tetrapelargonate are more preferred.

The cosmetic compositions according to the invention may also comprise one or more colouring agents or dyes, in quantities of preferably between 0.1% and 35% by weight, more preferably between 0.1 and 30% by weight, even more preferably between 0.1 and 20% by weight.

The said colouring agents may be soluble or insoluble in water, soluble or insoluble in fats, mineral or organic, natural or synthetic, and have the function of colouring or opacifying the cosmetic composition. Examples of suitable colouring agents are pigments, lacquers or pearls, which may be used as such or after surface treatments intended for example to modify water-repellence or hydrophilic properties. The pigments include derivatives of metals of an inorganic nature, for example oxides of iron, cerium, chromium, titanium, zinc or zirconium, silicates (e.g. micas), sulfosilicates (e.g. ultramarine) and their combinations, and molecules of an organic nature, such as for example plant extracts. By the term "pearls" are meant special pigments capable of developing reflection and refraction phenomena with light, which may be iridescent or non-iridescent, either organic (such as guanine, CI 75170) or inorganic (such as bismuth oxychloride, CI 77163, or sericite, CI 77019).

The mixtures of the pelargonic acid esters in question have the particular advantage of encouraging the dispersion of pigments, whose colour they may help to intensify.

The cosmetic compositions according to the invention may also comprise one or more additives selected from those typically used in cosmetic compositions, such as for example antioxidants and/or vitamins, preservatives, pH modifiers, humectants, conditioners, chelating agents, flow modifiers, texturising agents, foam-forming agents, silicones, perfumes, essential oils, and active ingredients, in particular cosmetically and/or dermatologically active ingredients. Each additive may be present in quantities from 0 to 35%, preferably from 0 to 20% by weight, more preferably from 0 to 10%, with respect to the total weight of the cosmetic composition.

By the term "preservatives" according to the invention are meant natural or synthetic substances having the primary function of inhibiting the growth of microorganisms in the cosmetic composition. The list of permitted preservatives makes reference to Appendix V to EC Regulation 1223/2009. The maximum permitted percentages used, any limitations and methods of use may be found within the document. The most widely used preservatives include for example: benzoic acid, propionic acid, salicylic acid, sorbic acid and their salts, p-hydroxybenzoic acid, its salts and esters, dehydroacetic acid, potassium sorbate, phenoxyethanol, imidazolidinyl urea. In combination or as an alternative to the said preservatives the cosmetic compositions according to the invention may also contain other substances capable of contributing to inhibition of the growth of microorganisms such as for example honey, essential oils such as extracts of rosemary, *Melaleuca alternifolia* and thyme, and complexing agents such as EDTA.

Mixtures of at least two esters selected from neopentyl glycol dipelargonate, glycerol tripelargonate and pentaerythritol tetrapelargonate therefore find application in coloured or colourless cosmetic compositions for the care, make up, protecting from the sun and cleansing of the skin and skin appendages.

They may advantageously be used for the preparation of creams, milks, sun protection products, serums, butters, bath foams, shower gels, detergents, shampoos, leave-on products, balms, face packs and leave-ons for hair, foundation cream, mascara, lipstick, eye shadow, blushers and compacted powders.

EXAMPLES

The esters used in the following examples have been prepared using pelargonic acid originating from the oxidative cleavage of sunflower oil having a high oleic acid content. In particular pelargonic acid obtained according to the process described in patent application WO 2011080296 has been used at the end of stage c) of separation of the monocarboxylic acids from the triglycerides containing more than one acid function and subsequent rectification to remove the fraction comprising light monocarboxylic acids, such as described in Example 1. The pelargonic acid used has a purity of 99%.

Preparation of Neopentyl Glycol Dipelargonate, Glycerol Tripelargonate and Pentaerythritol Tetrapelargonate Esters The esterification reactions for synthesis of the three esters were carried out in the absence of catalyst and with a molar excess of pelargonic acid of 30% molar with respect to the polyol used (neopentyl glycol, glycerine or pentaerythritol). In order to favour the removal of esterification water the temperature of the acid/polyol mixtures was increased to 200-210° C. in the course of the reactions; once this temperature had been reached gradual vacuum was applied up to 100 mbar in order to favour conversion of the reagents. Once the reactions were complete, after a quantity of reaction water corresponding to the theoretical quantity had been obtained, the excess acid was recovered by evaporation, keeping the temperature around 180-200° C. with a vacuum of 5 to 10 mbar.

The products then underwent decolouring treatment with activated carbon and decolouring earth and neutralisation through the addition of a quantity of calcium hydroxide and water (in a 1:1 ratio by weight) of between 1 and 2% by weight with regard to each ester, heating to 60° C. with stirring for 30 minutes. After water had been completely removed by heating to 80-100° C. in a vacuum, a filtering earth (Celite 512; 1% by weight with respect to the ester) was added with stirring, and the liquid was filtered under vacuum on a bed of the same earth, obtaining a clear product.

Measurements of acidity made in accordance with standard ASTM D664 showed a residual acidity of less than 0.1 mg KOH/g for each of the three esters.

Preparation of Powder-Based Cosmetic Compositions

The binding agents of the product were weighed and placed together with liposoluble preservatives in a melter of suitable capacity provided with a heating jacket, within which they were then mixed. In the presence of components having a binding action in solid or semi-solid form, such as waxes and hydrogenated derivatives, the mixture was heated with constant stirring to reach or exceed the melting point of the products by around 5-10° C. All the powders (including texturising agents and pigments) were placed in a mill of suitable capacity, provided with a cooling system and underwent mixing cycles established on the basis of the nature of the powders. The cooling system was operated to contain the rise in temperature deriving from mixing.

Once it had been verified that the powders which had been mixed were homogenous, the previously prepared binding component was gradually added in a stream and a further mixing was carried out to bring about incorporation of the latter into the powders. Any pearlescent pigments were added during working in this stage and were subjected to a further mixing cycle. At the end of the production process the bound powder was discharged from the mill and sieved.

Examples of cosmetic compositions according to the invention are shown in the tables below. The list of ingredients (in accordance with the INCI nomenclature) and the percentage compositions by weight of each ingredient in relation to the total weight of the composition are indicated for each composition.

Examples 1 (comparison)-2

Stick Concealer

Ingredients:

| | INCI | Example 1 (comparison) | Example 2 |
|---|---|---|---|
| A | C12-15 alkyl benzoate | 25.54 | — |
| | Glycerol tripelargonate | — | 8 |
| | Pentaerythritol tetrapelargonate | — | 4 |
| | Neopentyl glycol dipelargonate | — | 32.52 |
| | Ethylhexyl Palmitate | 10.98 | — |
| | Isononyl Isononanoate | 8.00 | — |
| | Dimethicone | 4.00 | 4 |
| | Candelilla Cera | 2.99 | 2.99 |
| | Copernicia Cerifera (Carnauba) Wax | 2.00 | 2 |
| B | Aluminum Starch Octenylsuccinate | 4.00 | 4 |
| | Polyethylene | 6.00 | 6 |
| | Talc | 6.00 | 6 |
| | Stearic Acid | 2.00 | 2 |
| | Microcrystalline Wax | 1.75 | 1.75 |
| | Silica | 0.94 | 0.94 |
| | Synthetic Wax | 0.15 | 0.15 |
| | Kaolin | 2.00 | 2 |
| | Polyglyceryl-3 Diisostearate | 2.00 | 2 |
| | Trimethylsiloxyphenyl Dimethicone | 1.95 | 1.95 |

-continued

| | INCI | Example 1 (comparison) | Example 2 |
|---|---|---|---|
| | Sorbitan Sesquiisostearate | 1.95 | 1.95 |
| | CI 77891 (Titanium Dioxide) | 1.98 | 1.98 |
| | CI 77491 (Iron Oxides) | 2.59 | 2.59 |
| | CI 77492 (Iron Oxides) | 4.47 | 4.47 |
| | CI 77499 (Iron Oxides) | 0.24 | 0.24 |
| | CI 77007 (Ultramarines) | 3.77 | 3.77 |
| C | Isododecane | 2.50 | 2.5 |
| | Polymethyl Methacrylate | 2.00 | 2 |
| | Tocopheryl Acetate | 0.20 | 0.2 |

Preparation:

The ingredients in group A were placed in a mixer and heated to a temperature of 90° C. On reaching this temperature the ingredients in phase B were added with stirring, mixing until the mixture was completely homogeneous. Continuing to heat in order to hold the temperature at around 80° C., all the ingredients in group C were added in the order in which they are shown in the table, continuing to stir until a homogenous mixture was obtained. The mixture so obtained was then poured into moulds and allowed to cool.

The lipophilic cosmetic composition in stick form according to the invention (Example 2), in which the lipophilic component contains a ternary mixture of neopentyl glycol dipelargonate, glycerol tripelargonate and pentaerythritol tetrapelargonate (44.52% by weight in relation to the total for the composition), revealed the same properties as a comparison composition (Example 1) in which the same quantity of lipophilic component was replaced by C12-C15 alkyl benzoate, ethylhexyl palmitate and isononyl palmitate.

Examples 3 (comparison)-5

Compacted Powder-Based Composition (Bronzing Powder)

Ingredients:

| INCI | Example 3 (comparison) | Example 4 | Example 5 | Example 6 (comparison) |
|---|---|---|---|---|
| Talc | 81 | 81 | 81 | 81 |
| Octyldodecyl Stearoyl Stearate | 6 | — | — | 1 |
| Glycerol tripelargonate | — | 5 | — | 5 |
| Pentaerythritol tetrapelargonate | — | 2 | 2 | — |
| Neopentyl glycol dipelargonate | — | — | 5 | — |
| Magnesium Stearate | 3 | 3 | 3 | 3 |
| Ethylene/Acrylic Acid Copolymer | 2.5 | 1.5 | 1.5 | 2.5 |
| Sorbic Acid | 0.35 | 0.35 | 0.35 | 0.35 |
| Sodium Dehydroacetate | 0.35 | 0.35 | 0.35 | 0.35 |
| CI 77491 (Iron Oxides) | 2.1 | 2.1 | 2.1 | 2.1 |
| CI 77492 (Iron Oxides) | 3.4 | 3.4 | 3.4 | 3.4 |
| CI 77499 (Iron Oxides) | 0.6 | 0.6 | 0.6 | 0.6 |
| CI 77891 (Titanium Dioxide) | 0.7 | 0.7 | 0.7 | 0.7 |

The two powder-based compositions according to the invention containing a binary mixture of glycerol tripelargonate and pentaerythritol tetrapelargonate (Example 4) and a binary mixture of pentaerythritol tetrapelargonate and neopentyl glycol dipelargonate (Example 5) respectively were prepared as described above. As can be seen from comparison Example 6, when only one pelargonic acid ester (glycerol tripelargonate) is used as binding agent, it requires the presence of other binding agents of common use. Examples 4 and 5 show instead that, when mixtures of glycerol tripelargonate and pentaerythritol tetrapelargonate or of neopentyl glycol dipelargonate and pentaerythritol tetrapelargonate are used, no further binder is needed in the compacted powder-based composition, entirely replacing Octyldodecyl Stearoyl Stearate and partly replacing the ethylene/acrylic acid copolymer of Example 3 (comparison).

Examples 7 (comparison)-9

Loose Powder-Based Composition (Face Powder)

Ingredients:

| INCI | Example 7 (comparison) | Example 8 | Example 9 | Example 10 |
|---|---|---|---|---|
| Talc | 83.94 | 83.94 | 82.94 | 83.94 |
| Triticum Vulgare Starch | 5.5 | 5.5 | 5.5 | 5.5 |
| Glycerol tripelargonate | — | 3.5 | — | 1.7 |
| Pentaerythritol tetrapelargonate | — | 0.5 | 2.2 | 0.5 |
| Neopentyl glycol dipelargonate | — | — | 1 | — |
| Zinc Stearate | 2 | 2 | 2 | 2 |
| Octyldodecanol | 1.8 | — | 1.8 | 1.8 |
| Caprylic/Capryc Triglyceride | 1.7 | — | — | — |
| Simmondsia Chinensis Seed Oil | 0.5 | — | — | — |
| Tocopherol | 0.1 | 0.1 | 0.1 | 0.1 |
| Glyceryl Caprylate | 1.5 | 1.5 | 1.5 | 1.5 |
| Sodium Dehydroacetate | 0.35 | 0.35 | 0.35 | 0.35 |
| CI 77491 (Iron Oxides) | 0.15 | 0.15 | 0.15 | 0.15 |
| CI 77492 (Iron Oxides) | 0.44 | 0.44 | 0.44 | 0.44 |
| CI 77499 (Iron Oxides) | 0.02 | 0.02 | 0.02 | 0.02 |
| CI 77891 (Titanium Dioxide) | 2 | 2 | 2 | 2 |

Three powder-based compositions according to the invention, containing a binary mixture of glycerol tripelargonate and pentaerythritol tetrapelargonate (Examples 8 and 10) and a binary mixture of pentaerythritol tetrapelargonate and neopentyl glycol dipelargonate (Example 9) were prepared as described above. These proved to be equivalent to a comparison composition in which the pelargonic acid esters were replaced by esters, alcohols and oils commonly used in cosmetic compositions (octyldodecanol, triglyceride of caprylic/capric acid, jojoba oil (Example 7)).

Examples 11-14

Lipstick Evaluation

Four lipophilic cosmetic compositions were prepared in the form of lipsticks according to the following ingredients list:

| | INCI | Example 11 (comparison) | Example 12 (comparison) | Example 13 | Example 14 (comparison) |
|---|---|---|---|---|---|
| A | Candelilla cera | 10.00 | 10.00 | 10.00 | 10.00 |
| | Copernicia Cerifera Cera | 1.76 | 1.76 | 1.76 | 1.76 |
| | Cera alba | 8.82 | 8.82 | 8.82 | 8.82 |
| | Octyldodecanol | 12.19 | 12.19 | — | 12.19 |
| | Ethylhexyl Stearate | 6.12 | 6.12 | 6.12 | 6.12 |

-continued

| INCI | Example 11 (comparison) | Example 12 (comparison) | Example 13 | Example 14 (comparison) |
|---|---|---|---|---|
| Diisostearyl malate | — | 15.60 | — | 15.60 |
| Glycerol tripelargonate | — | — | 10.50 | — |
| Pentaerythritol tetrapelargonate | 15.60 | — | 52.30 | — |
| Polyglyceryl-2 Isostearate/Dimer Dilinoleate Copolymer | 4.71 | 4.71 | — | 4.71 |
| Pentaerythrityl Tetraisostearate | 30.30 | 30.30 | — | 20.30 |
| Phenyl Dimethicone | — | — | — | 10.00 |
| Tocopheryl acetate | 0.50 | 0.50 | 0.50 | 0.50 |
| B Synthetic wax, Red 7 Lake, Isopropyl Titanium triisostearate | 5.80 | 5.80 | 5.80 | 5.80 |
| Synthetic wax, Titanium Dioxide, Isopropyl Titanium triisostearate | 4.20 | 4.20 | 4.20 | 4.20 |

The four resulting compositions were subjected to a sensory evaluation. A panel of 20 individuals (women) was required to test the lipsticks and provide a rating from 1 to 5 on the properties listed in the table below.

Evaluation scale:
5: Excellent
4: Very good
3: Good
2: Fair
1: Poor

| Sensory evaluation | Example 11 (comparison) | Example 12 (comparison) | Example 13 | Example 14 (comparison) |
|---|---|---|---|---|
| Flowability | 4 | 3 | 5 | 3 |
| Fullness | 5 | 4 | 5 | 4 |
| Softness | 4 | 3 | 5 | 3 |
| Adherence | 4 | 3 | 4 | 3 |
| Uniformity of the film | 5 | 3 | 5 | 4 |
| Gloss effect | 4 | 4 | 5 | 5 |

The composition of Example 13, comprising a mixture of glycerol tripelargonate and pentaerythritol tripelargonate, showed a more intense and homogeneous color, due to good pigment dispersion, and a better adherence on lips than the compositions of Examples 12 and 14.

When compared to the composition of Example 11 comprising only pentaerythritol tetrapelargonate, the composition of Example 13 also revealed higher softness and spreadability and a superior gloss effect, comparable to that achieved by the composition of Example 14 which comprises phenyl dimethicone.

Example 15

UV Filters Solubility

The solubility of the chemical UV filter Benzophenone-3 (CAS N° 131-57-7, commercially available as UVASORB® MET from 3V Sigma) in a ternary mixture of neopentyl glycol dipelargonate, glycerol tripelargonate and pentaerythritol tetrapelargonate (in a weight ratio of 1:1:1) was tested and compared to the solubility in the individual ester pentaerythritol tetrapelargonate.

Various ratios of solute/solvent (5%, 10%, 20% and 30% by weight; total amount filter+solvent: 10g) were prepared in glass bottles in a water bath at 60° C. The solutions were then observed after a storage period of 2 hours at 20° C. to check for the formation of any sediment deposit. Once identified the solubility range, which ranged between 10-20% for each filter/solvent couple, the maximum concentration of soluble filter in each sample was determined by making repeated additions of lower amounts of the filter to the solutions at 10%, until the formation of precipitate was observed. Each addition was carried out at a temperature of 60° C. and followed by cooling. The solutions were allowed to stand at the constant temperature of 20° C. for two hours before checking for precipitation (by visual determination).

Results for each ester are shown in the table below:

| Filters solubility | % w/w, 20° C. |
|---|---|
| Pentaerythritol tetrapelargonate | 14 |
| Neopentyl glycol dipelargonate/Glycerol tripelargonate/Pentaerythritol tetrapelargonate Mixture | 19 |

The solubility value at 20° C. of Benzophenone-3 in pentaerythritol tetrapelargonate was of 14% w/w, while the corresponding solubility value of the same filter in the ternary mixture was of 19% w/w. The mixture of pelargonic acid esters according to the invention therefore revealed a surprisingly high ability to solubilize UV filters when compared to the one of the individual ester pentaerythritol tetrapelargonate.

The invention claimed is:

1. A cosmetic composition comprising a mixture of at least two esters selected from the group consisting of neopentylglycol dipelargonate, glycerol tripelargonate and pentaerythritol tetrapelargonate.

2. The cosmetic composition according to claim 1 comprising from 0.1% to 99% by weight of the said mixture, relative to the total weight of the cosmetic composition.

3. The cosmetic composition according to claim 1 being a lipophilic cosmetic composition and comprising water in quantities not exceeding 20%, one or more powder components and up to 20% by weight of the said mixture, relative to the weight of the cosmetic composition.

4. The cosmetic composition according to claim 1 being an aqueous cosmetic composition and comprising more than 20% by weight of a hydrophilic component comprising water, and up to 50% by weight of the said mixture, relative to the weight of the cosmetic composition.

5. The cosmetic composition according to claim 4 comprising up to 15% by weight of the said mixture and further comprising surfactants.

6. The cosmetic composition according to claim 1 further comprising an oil selected from the group consisting of esters, ethers, amides, alcohols and hydrocarbons of natural or synthetic origin or mixtures thereof, silicone oils, and mixtures thereof.

7. The cosmetic composition according to claim 1 comprising a member selected from the group consisting of butters waxes and mixtures thereof.

8. The cosmetic composition according to claim 1 comprising one or more oligomers.

9. The cosmetic composition according to claim 1 comprising one or more sun filters in quantities from 0.1% to 35% by weight.

10. The cosmetic composition according to claim 1 comprising a member selected from the group consisting of one or more coloring agents, one or more additives and mixtures thereof, wherein the one or more additives are selected from the group consisting of antioxidants, vitamins and mixtures thereof, preservatives, pH modifiers, humectants, conditioners, chelating agents, flow modifiers, texturizers, film-forming, silicones, perfumes, essential oils, and actives.

11. The cosmetic composition according to claim 10 wherein each of said coloring agents, additives and mixtures thereof is present in amounts from 0.1 to 35% by weight with respect to the total weight of the cosmetic composition.

12. The cosmetic composition according to claim 2 being a lipophilic cosmetic composition and comprising water in quantities not exceeding 20%, one or more powder components and up to 20% by weight of the said mixture, relative to the weight of the cosmetic composition.

13. The cosmetic composition according to claim 2 being an aqueous cosmetic composition and comprising more than 20% by weight of a hydrophilic component comprising water, and up to 50% by weight of the said mixture, relative to the weight of the cosmetic composition.

14. The cosmetic composition according to claim 2 further comprising an oil selected from the group consisting of esters, ethers, amides, alcohols and hydrocarbons of natural or synthetic origin or mixtures thereof, silicone oils, and mixtures thereof.

15. The cosmetic composition according to claim 3 further comprising an oil selected the group consisting of esters, ethers, amides, alcohols and hydrocarbons of natural or synthetic origin or mixtures thereof, silicone oils, and mixtures thereof.

16. The cosmetic composition according to claim 4 further comprising an oil selected from the group consisting of esters, ethers, amides, alcohols and hydrocarbons of natural or synthetic origin or mixtures thereof, silicone oils, and mixtures thereof.

17. The cosmetic composition according to claim 5 further comprising an oil selected from the group consisting of esters, ethers, amides, alcohols and hydrocarbons of natural or synthetic origin or mixtures thereof, silicone oils, and mixtures thereof.

18. A method for the preparation of a cosmetic composition selected from the group consisting of creams, milks, serums, butters, bath foams, shower gels, detergents, shampoos, leave-on, balms, hair masks and leave-on, foundations, mascaras, lipsticks, lip glosses, concealers, eye shadows, blushers, face powders, loose powders and compact powders, wherein the method comprises including in said cosmetic composition a mixture of at least two esters selected from the group consisting of neopentylglycol dipelargonate, glycerol tripelargonate; and pentaerythritol tetrapelargonate.

19. A method for the care, for the make-up, for the protection from the sun or and for the cleansing of the skin and or skin appendages which comprises applying to the skin or skin appendages a cosmetic composition according to claim 1.

* * * * *